United States Patent [19]

Iyer et al.

[11] Patent Number: 5,833,944
[45] Date of Patent: Nov. 10, 1998

[54] PROCEDURE FOR THE SOLID PHASE SYNTHESIS OF $^{35}$S-LABELED OLIGONUCLEOTIDES WITH 3H-1,2-BENZODITHIOL-3-ONE-1,1-DIOXIDE

[75] Inventors: Radhakrishnan P. Iyer; Sudhir Agrawal, both of Shrewsbury; Weitian Tan, Framingham, all of Mass.

[73] Assignee: Hybridon, Inc., Worcester, Mass.

[21] Appl. No.: 335,100

[22] Filed: Nov. 7, 1994

[51] Int. Cl.$^6$ ........................... A61K 51/00; A61M 36/14
[52] U.S. Cl. ............................. 424/1.81; 549/1; 424/1.65
[58] Field of Search ................................. 424/1.65, 1.53, 424/1.11, 1.49, 9.36, 1.81, 9.1; 534/14; 549/1; 530/330

[56] References Cited

U.S. PATENT DOCUMENTS

| | | | |
|---|---|---|---|
| 4,139,362 | 2/1979 | Rasheed et al. | 71/90 |
| 4,175,186 | 11/1979 | Rasheed et al. | 544/145 |
| 5,003,097 | 3/1991 | Beaucage et al. | 530/300 |
| 5,149,798 | 9/1992 | Agrawal et al. | 536/27 |

OTHER PUBLICATIONS

Rao and MacFarlane. Tetrahedron Letters, vol. 35, No. 36, pp. 6741–6744 (1994) "Solid Phase Synthesis of Phosphorothiolate Oligonucleotides Using Benzytriethylammonium Tetrathiomolybdate as a Rapid Sulfur Transfer Reagent".
Wyrzykiewicz and Ravikumar. Bioorganic & Medicinal Chemistry Letters, vol. 4, No. 12, pp. 1519–1522 (1994), Efficiency of Sulfurization in the Synthesis of Oligodeoxyribonucleotide phosphorothioates utilizing various sulfurizing reagents.
Hortmann et al. J. Org. Chem., vol. 43, No. 17, pp. 3374–3378 (1978) "3H–1,2–Benzodithiole Oxides: Studies Directed toward the Generation of O–Thiobenzoquinone Methide and Benzo[b]thiete".
Stawinski and Thelin. J. Org. Chem., vol. 56, pp. 5169–5175 (1991) "Nucleoside H–Phosphonates. 13. Studies on 3H–1, 2–benzodithiol–3–one Derivatives as Sulfuring reagents for H–Phosphonates and H–Phosphonothioate Diesters".
Iyer et al. J Org. Chem. (1990), 55, pp. 4693–4699, The Automated Synthesis of Sulfur Containing Oligodeoxyribonucleotides using 3H–1,2–benzodithiol–3–One 1,1–Dioxide as a sulfur transfer reagent.
Regan et al. Org. Prep. Proced. Int (1992), 24(4) pp. 488–492 Large–Scale Preparation of the Sulfur transfer reagent 3–H–1,2–benzodithiol–3–one 1,1,–dioxide.
Holum Elements of General, Organic, and Biological Chemistry, 9th edition, pp. 40–42.
The Merck Index, 9$_{th}$edition, p. 1162, Compound 8764.
Becaucage and Iyer. Tetrahedron, vol. 49, No. 10, pp. 1925–1963 (1993). "The Functionalization of Oligonucleotides Vici Phosphoramidite Derivatives".
Stawinski et al. Nucleosides and Nucleotides, vol. 10, No. 1–3, pp. 517–518 (1991). "Studies on Sulfurization of Nucleoside H–Phosphonate and H–Phosphonothioate Esters Using 3H–1,2–Benzodithiol–3–One 1,1–dioxide".

Iyer et al. J. Am. Chem. Soc., vol. 112, pp. 1253–1254, "3H–1,2–benzodithiole–3–one 1,1–Dioxide as an Improved Sulfurzing Reagent in the Solid–Phase Synthesis of Oligodeoxyribonucleoside Phosphorothioates".
Iyer et al. Tetrahedron Letters, vol. 35, No. 51, pp. 9521–9524 (1994), Synthesis of [$^{35}$S]3H–1, 2–benzodithiole–3–one–1,1–dioxide: Application in the Preparation of site Specifically 35S–labeled Oligonucleotides.
Graham et al. Nucleic Acid Research, vol. 21, No. 16 pp. 3737–3743. "Tritium labeling of antisense oligonucleotides by exchange with tritiated water".
Stein et al., Analytical Biochemistry 188, 11–16 (1990).
Zamecnik and Stephenson, Proc. Natl. Acad. Sci. USA 75, 280–284 (1978).
Agrawal et al., Trends in Biotech. 10, 152–158 (1992).
Uhlmann and Peyman, Chem. Rev. 90, 543 (1990).
See generally, Methods in Molecular Biology, vol. 20: Protocols for Oligonucleotides and Analogs, pp. 165–189 (S. Agrawal, Ed., Humana Press, 1993).
See generally, Oligonucleotides and Analogues: A Practical Approach, pp. 87–108 (F. Eckstein, Ed., 1991).
Khorana et al., J. Molec. Biol. 72, 209 (1972).
Reese, Tetrahedron Lett. 34, 3143–3179 (1978).
Beaucage and Caruthers, Tetrahedron Lett. 22, 1859–1862 (1981).
Beaucage and Iyer, Tetrahedron Lett. 48, 2223 (1992).
Agrawal and Goodchild, Tetrahedron Lett. 28, 3539–3542 (1987).
Connolly et al., Biochemistry 23, 3443 (1984).
Jager et al., Biochemistry 27, 7237 (1988).
Agrawal et al., Proc. Natl. Acad. Sci. USA 85, 7079–7083 (1988).
Padmapriya et al., Antisense Res. & Dev. 4, 185–199 (1994).
Andrad et al., Bioorg. & Med. Chem. Lett., pp. 2017–2022 (1994).
Agrawal et al., Proc. Natl. Acad. Sci. U.S.A. 88, 7595–7599 (1991).
Kawamura et al., Chem. Lett. 1231–1234 (1975).
McKibben and McClelland, J. Chem. Soc., 170–173 (1923).
M. Hudlicky, Oxidation in Organic Chemistry, ACS Monograph 186, 1990.

Primary Examiner—John Kight
Assistant Examiner—Dameron L. Jones
Attorney, Agent, or Firm—McDonnell Boehnen Hulbert & Berghoff

[57] ABSTRACT

This invention provides a novel compound for $^{35}$S-labelling oligonucleotides. The compound is $^{35}$S-3H-1,2-benzodithiol-3-one-1,1 dioxide (1)

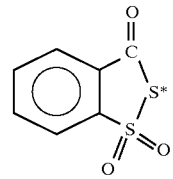

wherein the asterisk indicates the position of the $^{35}$S. Also provided is a method of synthesizing this compound, comprising first contacting $^{35}$S-thiobenzoic acid (4) with thiosalicylic acid (5) in acid medium to yield the condensation product, $^{35}$S-3 H 1,2-benzodithiol-3-one (2). $^{35}$S-3 H 1,2-benzodithiol-3-one (2) is then oxidized with a suitable oxidating agent such as trifuoroacetic acid and hydrogen perioxide to yield the desired product, $^{35}$S-3H-1,2-benzodithiol-3-one-1,1 dioxide (1). Any oligonucleotide susceptible to oxidative sulfurized by 3H-1,2-benzodithiol-3-one-1,1 dioxide can be labeled by $^{35}$S-3H-1,2-benzodithiol-3-one-1,1 dioxide (1). Accordingly, this invention also provides novel methods for $^{35}$S-labelling oligonucleotides. The compound and methods are useful for tracing biodistribution and degradation of antisense oligonucleotides in pharmacokinetic studies.

9 Claims, 6 Drawing Sheets

PROCEDURE FOR THE SOLID PHASE SYNTHESIS OF $^{35}$S-LABELED OLIGONUCLEOTIDES WITH 3H-1,2-BENZODITHIOL-3-ONE-1,1-DIOXIDE

BACKGROUND OF THE INVENTION

1. Field of the Invention

The invention relates to synthesis of $^{35}$S-labeled 3H-1,2 benzodithiol-3-one-1,1 dioxide (1) and its use in the preparation of site-specifically $^{35}$S-labeled oligonucleotides.

2. Description of the Prior Art

Since Zamecnik and Stephenson, *Proc. Natl. Acad. Sci. USA* 75, 280–284 (1978) first demonstrated virus replication inhibition by synthetic oligonucleotides, great interest has been generated in oligonucleotides as therapeutic agents. In recent years, the development of oligonucleotides as therapeutic agents and as agents of gene expression modulation has gained great momentum. The greatest development has been in the use of so-called antisense oligonucleotides, which form Watson-Crick duplexes with target mRNAs. Agrawal, *Trends in Biotechnology* 10, 152–158 (1992), extensively reviews the development of antisense oligonucleotides as antiviral agents. See also Uhlmann and Peymann, *Chem. Rev.* 90, 543 (1990).

Various methods have been developed for the synthesis of oligonucleotides for such purposes. See generally, *Methods in Molecular Biology*, Vol 20: *Protocols for Oligonucleotides and Analogs* (S. Agrawal, Ed., Humana Press, 1993); *Oligonucleotides and Analogues: A Practical Approach* (F. Eckstein, Ed., 1991); Uhlmann and Peyman, supra Early synthetic approaches included phosphodiester and phosphotriester chemistries. Khorana et al., *J. Molec. Biol.* 72, 209 (1972) discloses phosphodiester chemistry for oligonucleotide synthesis. Reese, *Tetrahedron* 34, 3143–3179 (1978), discloses phosphotriester chemistry for synthesis of oligonucleotides and polynucleotides. These early approaches have largely given way to the more efficient phosphoramidite and H-phosphonate approaches to synthesis. Beaucage and Caruthers, *Tetrahedron Lett.* 22, 1859–1862 (1981 (reviewed in Beaucage and Iyer, *Tetrahedron* 48, 2223 (1992)), discloses the use of deoxynucleoside phosphoramidites in polynucleotide synthesis. Agrawal and Zamecnik, U.S. Pat. No. 5,149,798 (1992), discloses optimized synthesis of oligonucleotides by the H-phosphonate approach.

Both of these modern approaches have been used to synthesize oligonucleotides having a variety of modified internucleotide linkages. Agrawal and Goodchild, *Tetrahedron Lett.* 28, 3539–3542 (1987), report synthesis of oligonucleotide methylphosphonates using phosphoramidite chemistry. Connolly et al., *Biochemistry* 23, 3443 (1984), discloses synthesis of oligonucleotide phosphorothioates using phosphoramidite chemistry. Jager et al., *Biochemistry* 27, 7237 (1988), discloses synthesis of oligonucleotide phosphoramidates using phosphoramidite chemistry. Agrawal et al., *Proc. Natl. Acad. Sci. USA* 85, 7079–7083 (1988), discloses synthesis of oligonucleotide phosphoramidates and phosphorothioates using H-phosphonate chemistry.

The use of 3H-1,2 benzodithiol-3-one-1,1 dioxide (1) as a sulfurizing reagent, (Iyer et al., *J. Am. Chem. Soc.* 112, 1253–1254 (1990)) in conjunction with phosphoramidite chemistry (Beaucage and Caruthers, *Tetrahedron Lett.* 22, 1859–1862 (1981) and Beaucage and Iyer, *Tetrahedron* 48, 2223–2311 (1992)) is now well established for the routine synthesis and large-scale manufacture of a variety of oligonucleoside phosphorothioates. Use of this reagent for the synthesis of methylphosphonothioates and other analogs has been reported. Padmapriya et al., *Antisense Res. & Dev.* 4, 185–199 (1994) and Andrad et al., *Bioorg. & Med. Chem. Lett.* pp. 2017–2022 (1994). For biological studies, $^{35}$S-labeled oligonucleoside phosphorothioates are prepared using the alternate chemistry viz., H-phosphonate chemistry. Garegg et al., *Chem. Scr.* 25, 280–282 (1985). It is difficult to achieve site-specific labeling of phosphorothioates using H-phosphonate chemistry, however, and it is inconvenient to carry out preparation of $^{35}$S-labeled oligonucleoside phosphorothioate constructs, such as those with (a) mixed ribonucleotide-deoxyribonucleotide population ("hybrid oligos"), (b) heterogeneous backbones, e.g., deoxyribonucleotide-methyl phosphonate ("chimeric oligos") and (c) mixed phosphodiester-phosphorothioate (PO-PS) backbones. In order to ensure stereochemically "uniform" product, it is desirable to follow the same chemistry both for synthesis and biological evaluation. The disadvantages of using elemental sulfur have also been recognized. Iyer et al., *J. Am. Chem. Soc.* 112, 1253–1254 (1990) and Iyer et al., *J. Org. Chem.* 55, 4693–4698 (1990).

In vivo pharmacokinetic studies of pharmalogical compounds, e.g., antisense oligonucleotide phosphorothioates (Agrawal et al., *Proc. Natl. Acad. Sci. U.S.A.* 88, 7595–7599 (1991)) requires labelling the compounds to enable detection. $^{35}$S-labelling is an established and widespread technique. In view of the aforementioned difficulties in synthesizing $^{35}$S-labeled oligonucleoside phosphorothioate constructs, improved methods are desirable.

SUMMARY OF THE INVENTION

The present invention provides new compounds and improved methods for synthesizing $^{35}$S-labeled oligonucleoside phosphorothioates. This invention comprises several aspects. In the first aspect, the present invention provides a novel compound useful for synthesizing oligonucleotide phosphorothioates labelled with $^{35}$S. This compound, $^{35}$S-3H-1,2-benzodithiol-3-one-1,1 dioxide (1), has the structure wherein the asterisk denotes the $^{35}$S label.

In a second aspect of the invention, a new method of synthesizing $^{35}$S-3H-1,2-benzodithiol-3-one-1,1 dioxide (1) is provided. An important consequence of this method is that it allows for the preparation of a variety of $^{35}$S-labeled oligonucleotide phosphorothioates and thereby facilitates pharmacokinetic studies of these compounds.

Figure 2:
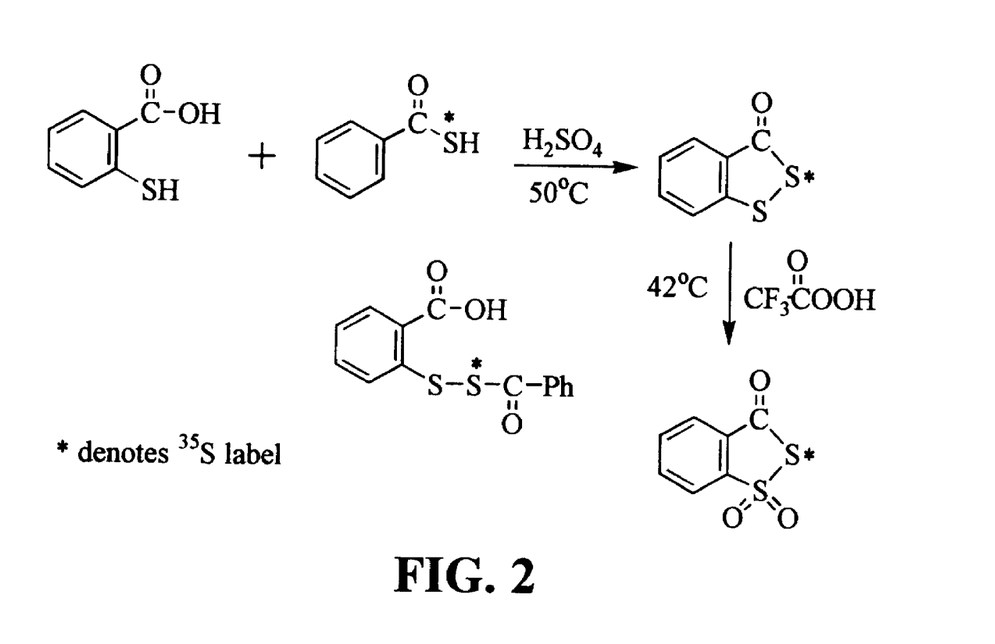
FIG. 2 depicts the synthesis of $^{35}$S-3H-1,2-benzodithiol-3-one-1,1 dioxide (1) from $^{35}$S-thiobenzoic acid (4) and thiosalicylic acid (5) via the intermediate $^{35}$S-3H-1,2-benzodithiol-3-one (2).

The method of synthesizing $^{35}$S-3H-1,2-benzodithiol-3-one-1,1 dioxide (1) is depicted in FIG. 2 and comprises first contacting $^{35}$S-thiobenzoic acid (4) with thiosalicylic acid (5) to yield the condensation product, $^{35}$S-3 H 1,2-benzodithiol-3-one (2). $^{35}$S-3 H 1,2-benzodithiol-3-one (2) is then oxidized to yield the desired product, $^{35}$S-3H-1,2-benzodithiol-3-one-1,1 dioxide (1).

Figure 3:
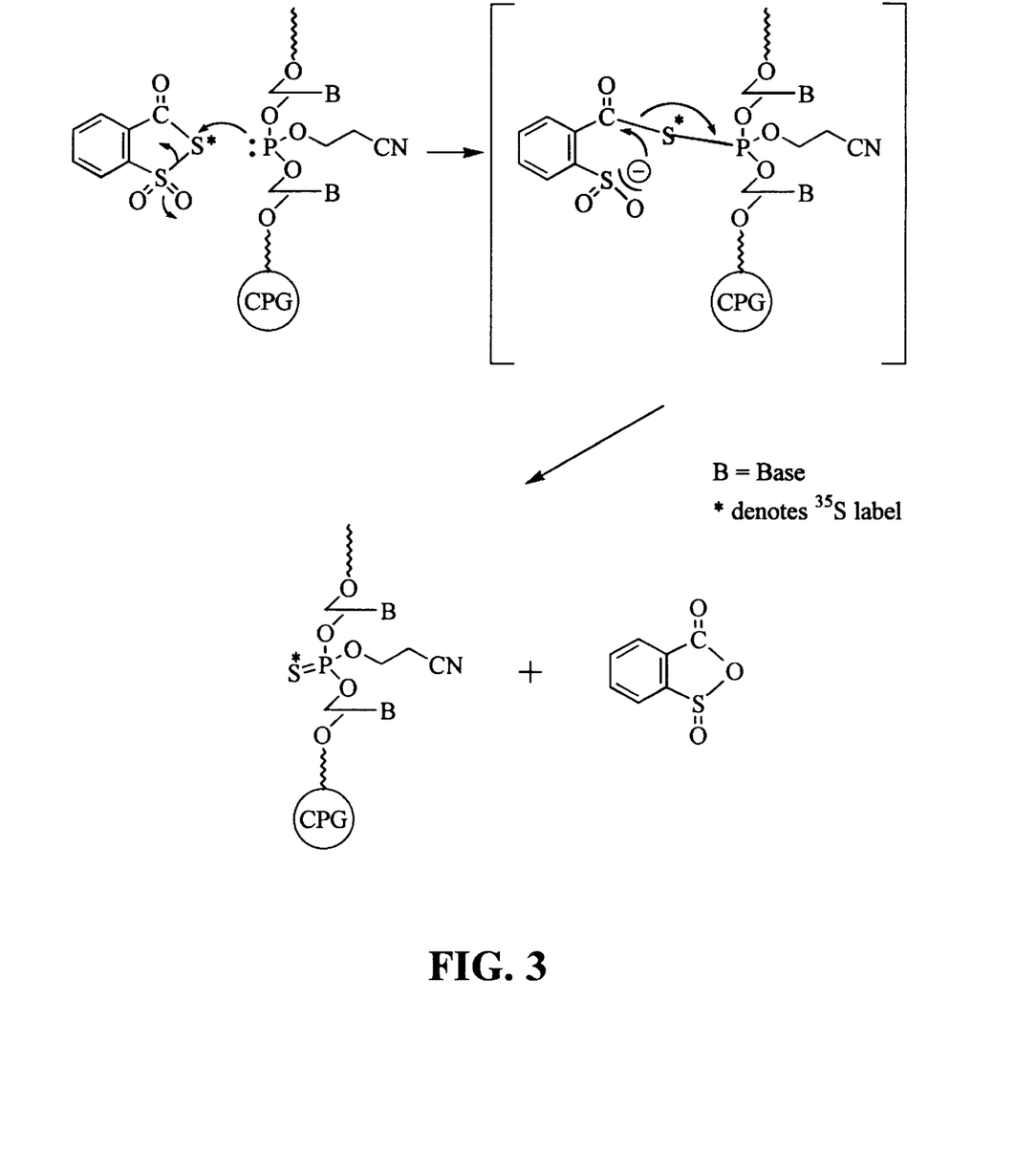
FIG. 3 depicts the $^{25}$S labelling of an oligonucleotide synthesized by the phosphoramidate method.

In the third aspect of the invention, a new method of synthesizing $^{35}$S-labelled oligonucleotides is provided. This method comprises contacting $^{35}$S-3H-1,2-benzodithiol-3-one-1,1 dioxide (1) with an oligonucleotide susceptable to oxidative sulfurization. The method of $^{35}$S labelling an oligonucleotide synthesized via the phosphoramidite method is depicted in FIG. 3. Other methods are contemplated, however, such as oxidative sulfurization of alkyl- and/or aryl-phosphites to yield the corresponding $^{35}$S-labelled alkyl- and/or aryl-phosphonothioate.

Those skilled in the art will appreciate that $^{35}$S-3H-1,2-benzodithiol-3-one-1,1 dioxide (1) can be used for any purpose and in any way that its unlabelled analog, 3H-1,2-benzodithiol-3-one-1,1 dioxide, can be used.

The foregoing merely summarizes certain aspects of the present invention and is not intended, nor should it be construed, to limit the invention in any way.

All patents and other references cited in this specification are hereby incorporated by reference in their entirety.

DESCRIPTION OF THE PREFERRED EMBODIMENTS

Because of the ever-increasing interest in antisense oligonucleotides as therapeutic agents, there is a need to provide methods whereby the pharmacokinetic properties of these compounds can be tested. It is necessary to determine biodistribution, as well as to determine the half-lives and degradation products. One method of accomplishing these tasks is to label the oligonucleotides with $^{35}$S, a common isotopic label used for tracing and detecting biological compounds.

The present invention provides a new compound useful for synthesizing $^{35}$S-labelled antisense oligonucleotides, a new method of synthesizing the compound and new methods for $^{35}$S-labelling oligonucleotides.

The first aspect of the invention comprises a new compound, $^{35}$S-3H-1,2-benzodithiol-3-one-1,1 dioxide (1), having the following structure wherein the asterisk indicates the position of the $^{35}$S radionucleotide.

The non-radiolabelled analog, 3H-1,2-benzodithiol-3-one-1,1 dioxide, is known (e.g., Beaucage, Regan and Iyer U.S. Pat. No. 5,003,097 (Beaucage et al. '097) and Iyer et al., J. Am. Chem. Soc. and J. Org. Chem., supra), but the $^{35}$S-labelled compound has never before been synthesized.

Those skilled in the art will appreciate that $^{35}$S-3H-1,2-benzodithiol-3-one-1,1 dioxide (1) can be used for the same purposes and in the same manner as its non-radiolabelled counterpart. A second aspect of the invention comprises a new method of synthesizing $^{35}$S -3H-1,2-benzodithiol-3-one-1,1 dioxide. This method is a modification of the method of Beaucage et al. '097, for example. An important benefit of this method is that it enables production of $^{35}$S-3H-1,2-benzodithiol-3-one-1,1 dioxide (1). In contradistinction to prior art methods, the method of this invention uses a reactant in which the $^{35}$S label is easily incorporated.

The prior art teaches that the precursor to 3H-1,2-benzodithiol-3-one-1,1 dioxide, 3H-1,2-benzodithiol-3-one, can be produced by mixing 2-thiolbenzoic acid and thiolacetic acid in sulfuric acid. E.g., Beaucage et al. '097. To have the $^{35}$S in the appropriate position in the final product using this method, it is necessary to incorporate the $^{35}$S in the thiolacetic acid. We attempted the preparation of $^{35}$S-thiolacetic acid by a high temperature (125° C.) exchange reaction between thiolacetic acid and elemental $^{35}$S using a reported procedure. Kawamura et al., Chem. Lett. 1231–1234 (1975). The high volatility (b.p. 81° C.) and vapor pressure of thiolacetic acid posed problems, however, when using $^{35}$S with high specific activity (32 mCi/μmol), and the $^{35}$S-labelled thiolacetic acid could not be isolated with high specific activity.

Figure 1:
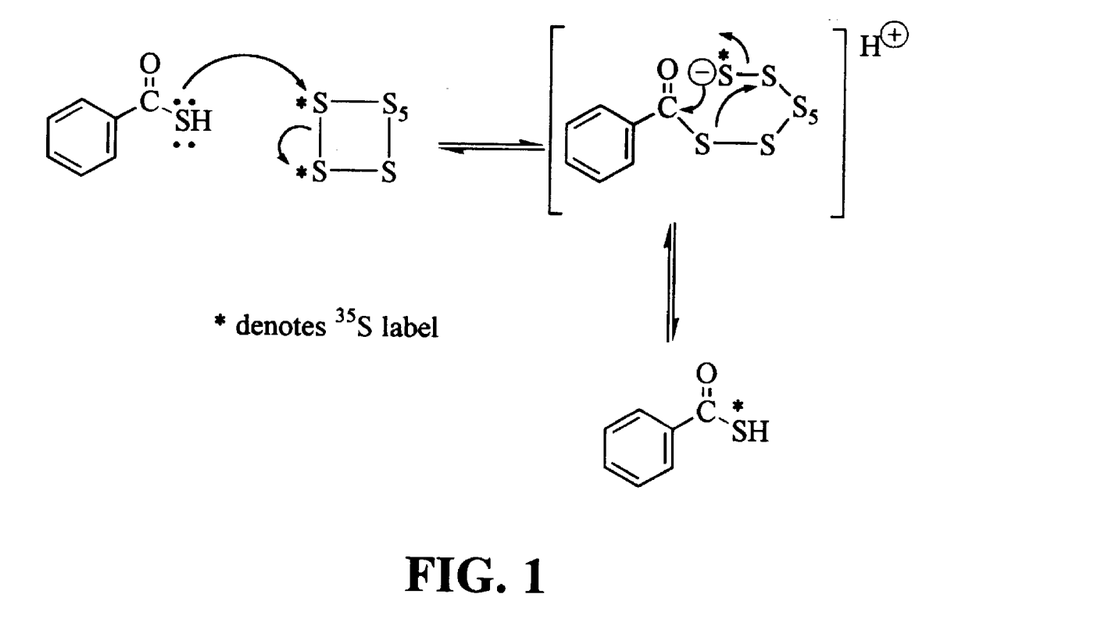
FIG. 1 depicts the synthesis of $^{35}$S-thiobenzoic acid (4) from $^{35}$S elemental sulfur and thiobenzoic acid.

To circumvent the difficulty encountered by trying to $^{35}$S label thiolacetic acid, we sought a thiol acid with a higher boiling point and lower vapor pressure. The commercially available thiobenzoic acid (4) seemed an ideal candidate. Before using $^{35}$S-4 in the preparation of 1, we validated the use of 4 in the synthesis of 1, by preparing $^{35}$S-3H-1,2-benzodithiol-3-one (2), the precursor to 1 (FIG. 2). Although we do not wish to be bound by any theory, and, indeed, this synthetic method does not depend on any theory, presumably 2 is formed (McKibben and McClelland, J. Chem. Soc. 170–173 (1923)) via the intermediate 3:

A longer time (4 hours) was required for completion of the reaction, although the yield (ca. 60%) was somewhat lower than when thiolacetic acid is use (ca. 80%). A crystallized sample of 2, thus synthesized, was identical in all respects (m.p., $^1$H-NMR and $^{13}$C-NMR) to that obtained by the reported procedure using thiolacetic acid Iyer et al., J. Am. Chem. Soc. 112, 1253–1254 (1990) and Iyer et al. J. Org. Chem. 55, 4693–4698 (1990). Having demonstrated the feasibility of using 4 in the preparation of 2, $^{35}$S-4 was conveniently prepared (FIG. 1) in high radiochemical yield (78%). $^{35}$S-4 thus obtained was converted to $^{35}$S-2 (FIG. 2), which, when subjected to carefully controlled oxidation, using hydrogen peroxide in trifluoroacetic acid. Iyer et al., J. Am. Chem. Soc. 112, 1253–1254 (1990) and Iyer et al. J. Org. Chem. 55, 4693–4698 (1990). It is important to avoid use of excess $H_2O_2$. The desired product $^{35}$S-1 as a white crystalline solid in 30% chemical yield (based on the amount of 5 used) and having a specific activity of 90 μCi/μmol. The reaction mixture should be worked up immediately after its completion to avoid decomposition of $^{35}$S-1.

Thus, the synthetic method according to this aspect of the invention comprises first contacting $^{35}$S-thiobenzoic acid (4)

with thiosalicylic acid (5) to yield the condensation product, $^{35}$S-3 H 1,2-benzodithiol-3-one (2). This reaction is acid catalyzed. In a preferred embodiment sulfuric acid is used, although any suitably strong acid may be used. $^{35}$S-3H 1,2-benzodithiol-3-one (2) is then oxidized to yield the desired product, $^{35}$S-3H-1,2-benzodithiol-3-one-1,1 dioxide (1). Any suitably strong oxidizing agent may be used, e.g., hydrogen peroxide and trifluoroacetic acid, trifluoro peroxyacetic acid or other oxidizing agents such as oxone, sodium periodate NaOCl, RuCl$_3$ and reagents used in the oxidation of sulfide to sulfone. See, e.g., M. Hudlicky, *Oxidation in Organic Chemistly,* ACS Monograph 186, 1990. In a preferred embodiment, oxidation is accomplished with hydrogen peroxide and trifluoroacetic acid. This scheme is depicted in FIG. 2.

The third aspect of the present invention comprises a new method for $^{35}$S-labelling oligonucleotides. The method can be used to selectively place the $^{35}$S at any desired internucleoside linkage. Anywhere from one to all internucleoside linkages may be labelled with $^{35}$S. The method comprises contacting $^{35}$S-3H-1,2-benzodithiol-3-one-1,1 dioxide (1) with an oligonucleotide susceptible to oxidative sulfurization. In a preferred embodiment, the oligonucleotide is synthesized by the phosphoramidite method, and $^{35}$S-3H-1,2-benzodithiol-3-one-1,1 dioxide (1) is contacted with the oligonucleotide having one or more β-cyanoethyl phosphotriester internucleoside linkages under standard conditions known in the art. In another preferred embodiment, an oligonucleotide having one or more alkyl- and/or aryl-phosphite internucleotide linkages is contacted with $^{35}$S-3H-1,2-benzodithiol-3-one-1,1 dioxide (1) to yield the corresponding $^{35}$S-labelled alkyl- and/or aryl-phosphonothioate. This reaction, using the non-radiolabeled oxidative sulfurization agent, is taught by Padmapriya et al., supra.

Those of skill in the art will appreciate that $^{35}$S-3H-1,2-benzodithiol-3-one-1,1 dioxide (1) can be used to $^{35}$S-label any compound that is capable of being sulfurized by the unlabeled analog 3H-1,2-benzodithiol-3-one-1,1 dioxide. For instance, the present method is capable of $^{35}$S labelling carbohydrates, proteins, and any macromolecule into which one can incorporate an $^{35}$S label by oxidative thiolation. Thus, RNA can be labelled with $^{35}$S in a site-specific manner, as can phosphopeptides. Phosphorothioate and sulfur analogs of phospholipids, glycerophospholipids, and phosphocarbohydtrates (e.g., myoinositol phosphates or their conjugates with other macromolecules) can also be labeled with 35S. 35S can be inserted into thiophosphates and thiotriphosphates (e.g., ATP) and then incorporated into any molecule using chemical or enzymatic phosphorylation reactions.

The following examples are provided for illustrative purposes only and are not intended, nor should they be construed, to limit the invention in any way.

EXAMPLES

Example 1

Synthesis of $^{35}$S-3H-1,2-benzodithiol-3-one-1,1 dioxide (1)

Synthesis of 35S-3H-1,2-benzodithiol-3-one (2)

A solution of $^{35}$S (5 mCi in 100 μl of toluene) (Amersham, England) and 6.5 μl (55 μmol) of unlabelled thiobenzoic acid (Aldrich, Milwaukee, Wis.) were placed in a 1.5 ml Eppendorf tube and the contents heated at 97° C. for 5 hours. The solution was evaporated to dryness under argon and 5 mg of thiosalicylic acid (Aldrich, Milwaukee, Wis.) was added. The reaction mixture was cooled to 0° C. and sulfuric acid (98%, 50 ml, (J. T. Baker, Phillipsburg, N.J.) was added. The mixture was kept at 50° C. for 3 hours. The resulting brown reaction mixture was cooled to −78° C. and 600 μl of water was added. The solution was extracted with methylene chloride (4×3 ml) (VWR, Westchester, Pa.) and the organic layer washed with Na$_2$CO$_3$ (5%, 2×2 ml) (EM Science, Gibbstown, N.J.). The organic layer was evaporated to dryness under a stream of argon to give a yellow solid. The material was then dissolved in 3 ml of warm hexane (J. T. Baker, Phillipsburg, N.J.), and after centrifugation the supernatant solution was evaporated to dryness under argon to give a pale yellow solid (4 mg, 44% yield). This material could be used in the next step without additional purification and was stored at −20° C. until ready to use.

Synthesis of $^{35}$S-3H-1,2-benzodithiol-3-one-1,1 dioxide (1) from$^{35}$S-3H-1,2-benzodithiol-3-one (2)

To a 1.5 ml Eppendorf tube containing 4 mg of $^{35}$S-3H-1,2-benzodithiol-3-one (2) (prepared as described above), both of which had been cooled to 0° C., 25 ml of trifluroacetic acid (Aldrich, Milwaukee, Wis.) and 12 ml 30% hydrogen peroxide (Aldrich, Milwaukee, Wis.) were added. The reaction mixture was warmed to 42° C. After about 2 hours (as monitored by TLC, silica gel, chloroform Iyer et al., *J. Org. Chem.*), the reaction mixture was cooled to 0° C. and 300 ml of water added. A white precipitate of $^{35}$S-3H-1,2-benzodithiol-3-one-1,1 dioxide (1) was immediately formed. The slurry was centrifuged and the precipitate washed with water (2×300 μl) and dried in vacuo to give 2 mg of $^{35}$S-3H-1,2-benzodithiol-3-one-1,1 dioxide (1) (total activity of 350 μCi, specific activity 90 μCi/μmol).

A solution of $^{35}$S-3H-1,2-benzodithiol-3-one-1,1 dioxide (1) in anhydrous acetonitrile (2 mg, 90 μCi/μmol in 200 ml acetonitrile) was used for the oxidative sulfurization reaction described below. The solution could be stored at −20° C. until ready for use.

Example 2

Synthesis of $^{35}$S-labelled Oligonucleotides

In order to demonstrate the use of $^{35}$S-3H-1,2-benzodithiol-3-one-1,1 dioxide (1) in the preparation of oligonucleotides, we prepared $^{35}$S-d[TpsT] (where the "ps" stands for phosphorothioate internucleoside linkage) on a 0.1 μmol scale in an automated DNA synthesizer using phosphoramidite chemistry. Beaucage and Caruthers, *Tetrahedron Lett.* 22, 1859–1862 (1981) and Beaucage and Iyer, *Tetrahedron* 48, 2223–2311 (1992). To incorporate the $^{35}$S label, the synthesis cycle was interrupted after the formation of the internucleotidic phosphite linkage. The CPG was removed from the column and treated with a solution of (15 ml, 90 μCi/μmol, 30 min.) followed by treatment with a solution of "cold" (i.e., non-$^{35}$S labelled) 3H-1,2-benzodithiol-3-one-1,1 dioxide (2% in acetonitrile, 100 ml, 10 min). A sample of the (TpsT) prepared under the exact conditions employing "non-radioactive" 1 revealed that the conversion of TpsT was >99%.

Figure 4A:
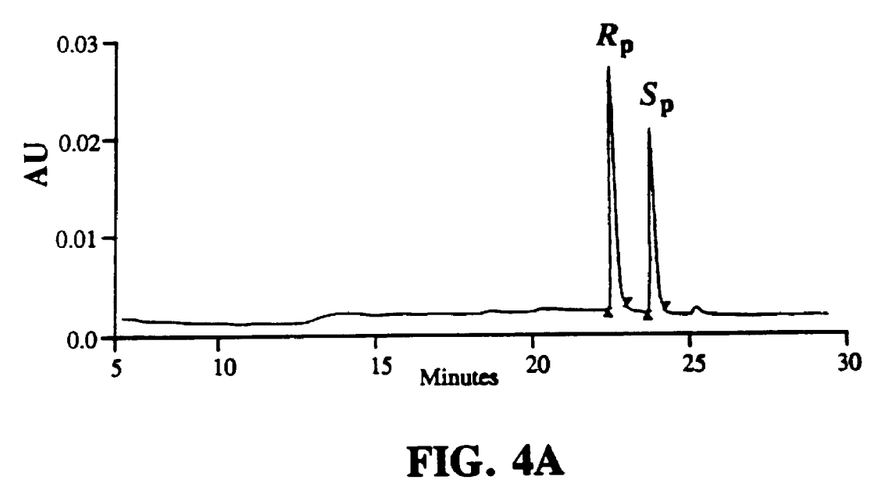
FIG. 4 is a RP-HPLC profile of $^{35}$S-R$_p$-d[TpsT] and $^{35}$S-S$_p$-d[TpsT] by UV detection at λ=260 nm (Panel A) and by flow scintillation Analysis (Panel B).
Figure 4B:
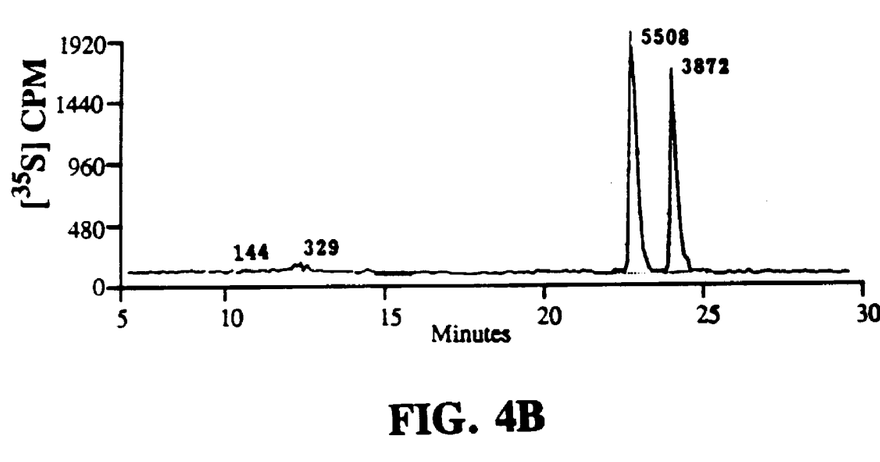

The oxidative-sulfurization was quantitative as determined by "trityl assays" conducted during the synthesis. Agrawal, *Protocols in Molecular Biology,* supra. After cleavage from the CPG and phosphate deprotection with aqueous ammonium hydroxide (30%, 2 hours, 35° C.) the dimer was examined by polyacrylamide gel electrophoresis (PAGE, 20%). The autoradiographic image was superimposable on its UV-shadowed band. When subjected to reverse-phase HPLC employing a UV detector interfaced with a radiochemical detector, its radioactivity profile was superimposable on the UV-absorbing peaks, corresponding to retention times of Rp-$^{35}$S-d[TpsT] (retention time=22.7 min) and Sp-$^{35}$S-d[TpsT] (retention time=24.0 min) (FIG. 4, Panel A). ("Rp" and "Sp" represent the two configurations at the chiral phosphorous center.) Detection by flow scintillation analysis is display in FIG. 4, Panel B. HPLC analysis was done with a Waters column (Milford, Mass.) equipped with a photodiode array UV detector interfaced with a Radiomatic (Meriden Ct., Mass.) 500 TR v3.00 radiochemical detector using 8NV $C_{18}$ 4$\mu$ Radial Pak (Waters, Milford, Mass.) cartridge column, gradient (100% A to 60% B over 60 minutes) of buffer A (0.1M $CH_3CO_2NH_4$) and buffer B (80:20, $CH_3CN$:0.1M $CH_3CO_2NH_4$), flow rate 1.5 ml/min.

Figure 5:
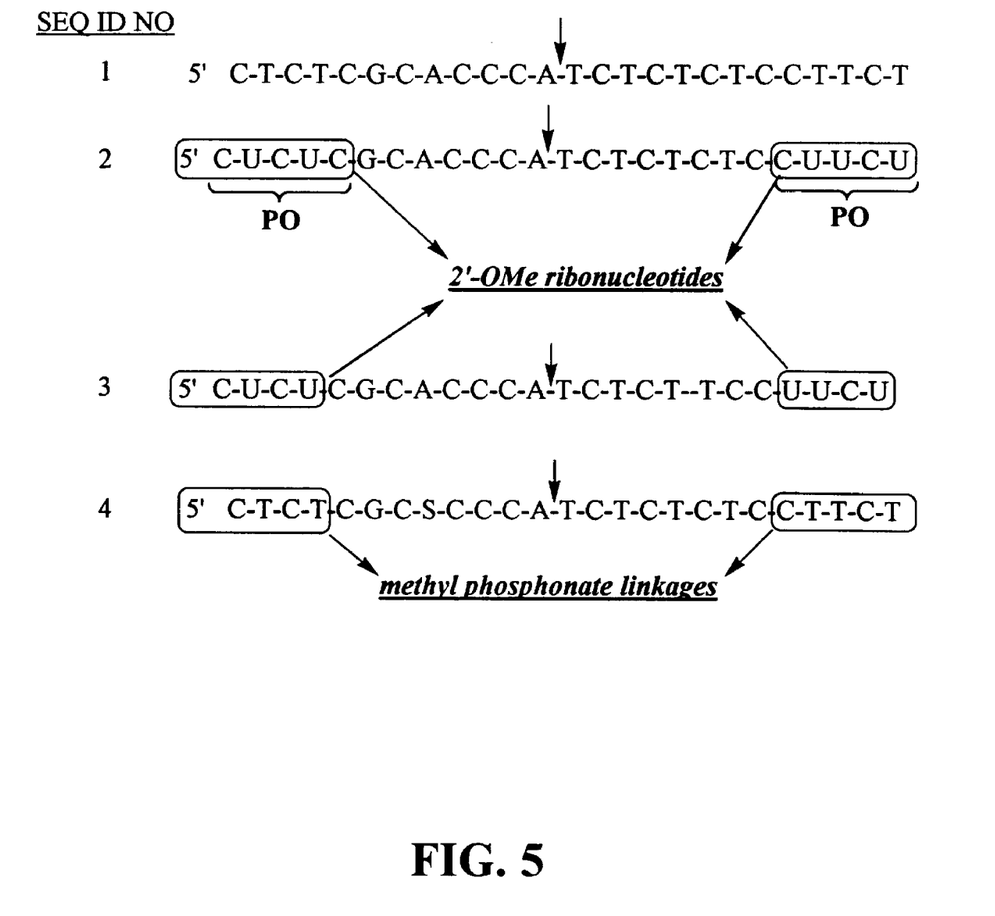
FIG. 5 displays $^{35}$S-labelled oligonucleotides synthesized according to the methods of the present invention.

We then prepared on a 1 $\mu$mol scale a variety of oligonucleotides (SEQ ID NOs 1–4) bearing a pre-determined site of incorporation of the $^{35}$S label. As displayed in FIG. 5, all internucleotide linkages are phosphorothioates, except as indicated. The arrows indicate the $^{35}$S-label site. For site specific incorporation of the $^{35}$S label, the synthesis cycle was interrupted at the desired point and treated with $^{35}$S-3H-1,2-benzodithiol-3-one-1,1 dioxide (1) (50$\mu$l, 90 $\mu$Ci/$\mu$mol, 30 min) as before. The oxidative-sulfurization was quantitative as determined by "trityl assays" conducted during the synthesis.

Figure 6:
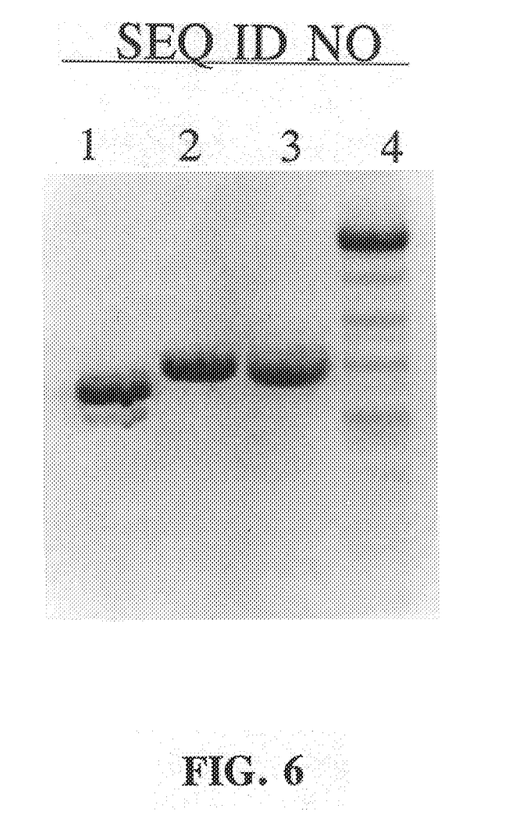
FIG. 6 displays and autoradiogram of oligonucleotides SEQ. ID NOs. 1–3 (purified) and SEQ. ID. NO. 4 (crude) subjected to PAGE.

After deprotection with ammonium hydroxide (30%, 10 hour, 55° C.), the crude oligonucleotides (SEQ ID NOs 1–4) were purified by preparative PAGE, desalted by Sephadex G-25 chromatography, lyophilized dry and subjected to analytical PAGE (FIG. 6). The oligonucleotides (SEQ ID NOs 1–4) thus obtained had a specific activity of about 23–25 $\mu$Ci/$\mu$mol.

Figure 7A:
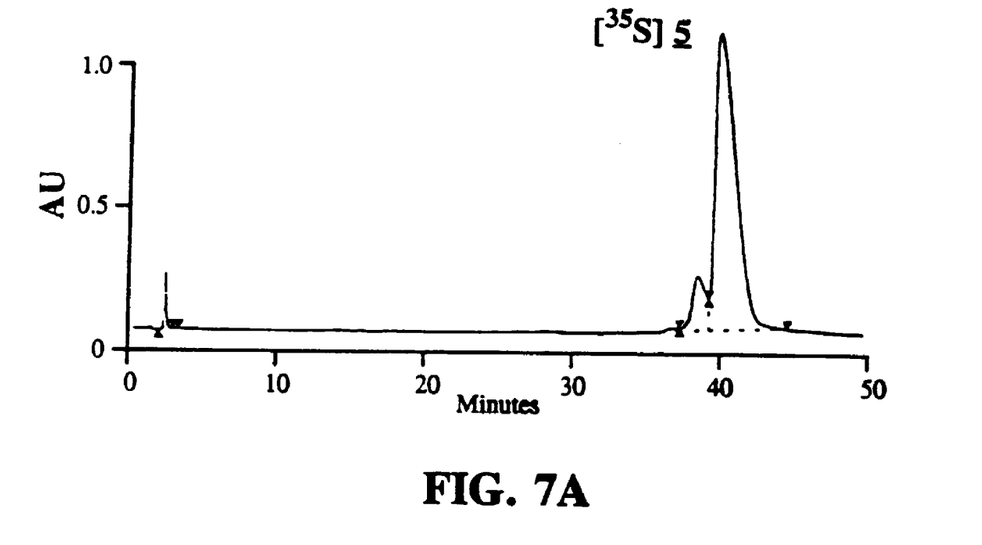
FIG. 7 displays an ion-exchange HPLC profile of $^{35}$S-labelled SEQ. ID. NO. 1 as detected by UV absorbance at λ=260 nm (Panel A) and by flow scintillation analysis (Panel B).
Figure 7B:
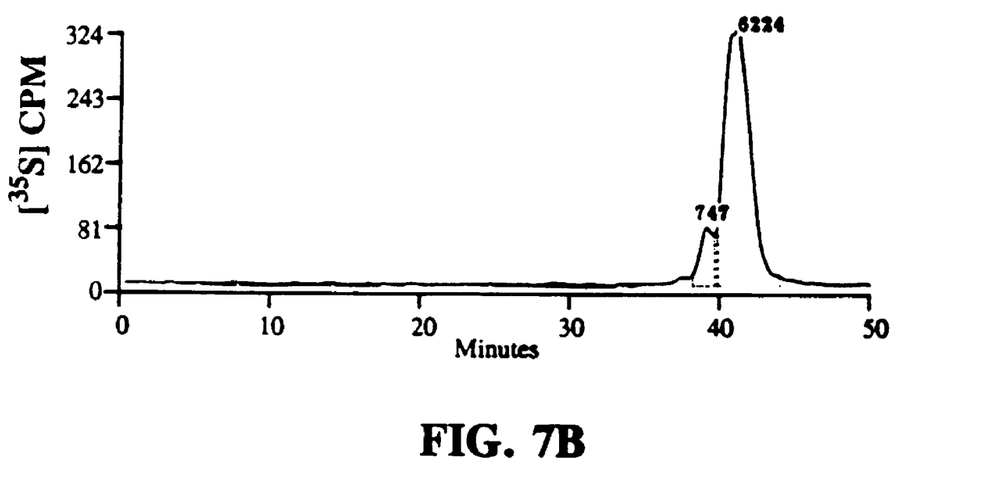

We subjected $^{35}$S-labelled SEQ. ID. NO. 1 to ion-exchange HPLC and detected the eluant by UV detection at $\lambda$=260 mn (FIG. 7, Panel A) and by flow scintillation analysis (FIG. 7, Panel B). Ion-exchange HPLC was done using a GEN-PAK FAX column (4.6×100 mm) at 65° C. using a gradient (80% A to 100% B over 50 min.) of Buffer A (25 mM Tris HCL, pH 8.5, 10% $CH_3CN$) to Buffer B (25 mM Tris HCl, 2M LiCl, pH 8.5, 10% $CH_3CN$) and a flow rate of 0.5 ml/min.

We claim:

1. A $^{35}S$ containing compound having the structure:

wherein the asterisk indicates the $^{35}S$.

2. A method of synthesizing the compound of claim 1 comprising contacting thiosalicylic acid with $^{35}S$-thiobenzoic acid in acid medium and oxidizing the reaction product.

3. The method of claim 2 wherein oxidation of the reaction product is accomplished with an oxidizing agent selected from the group consisting of trifluoroacetic acid and hydrogen peroxide, trifluoroperoxyacetic acid, oxone, sodium periodate, NaOCl, and RuCl$_3$.

4. A method of synthesizing the compound of claim 1 comprising oxidizing $^{35}S$-3H-1,2-benzodithiol-3-one, which has the structure wherein the asterisk indicates the position of the $^{35}S$.

5. The method of claim 4 wherein the oxidizing agent is a mixture of trifuoroacetic acid and hydrogen peroxide.

6. The method of claim 4 wherein the $^{35}S$-3H-1,2-benzodithiol-3-one is synthesized by contacting thiosalicylic acid with $^{35}S$-thiobenzoic acid in acid medium.

7. A method of $^{35}S$-labelling an oligonucleotide comprising contacting the compound of claim 1 with an oligonucleotide susceptible to oxidative sulfurization.

8. The method according to claim 7 wherein the oligonucleotide has from one to all β-cyanoethyl phosphoramidite internucleoside linkages.

9. The method according to claim 7 wherein the oligonucleotide has from one to all alkyl or aryl phosphite internucleoside linkages.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear     ( i i ) MOLECULE TYPE: other nucleic acid     ( i i i ) HYPOTHETICAL: NO     ( i v ) ANTI-SENSE: YES     ( x i ) SEQUENCE DESCRIPTION: SEQ ID NO:1:

C T C T C G C A C C     C A T C T C T C T C     C T T C T     2 5

( 2 ) INFORMATION FOR SEQ ID NO:2:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear     ( i i ) MOLECULE TYPE: other nucleic acid     ( i i i ) HYPOTHETICAL: NO     ( i v ) ANTI-SENSE: YES     ( x i ) SEQUENCE DESCRIPTION: SEQ ID NO:2:

C U C U C G C A C C     C A T C T C T C T C     C U U C U     2 5

( 2 ) INFORMATION FOR SEQ ID NO:3:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear (ii) MOLECULE TYPE: other nucleic acid (iii) HYPOTHETICAL: NO (iv) ANTI-SENSE: YES (xi) SEQUENCE DESCRIPTION: SEQ ID NO:3:

CUCUCGCACC CATCTCTCTC CUUCU                                                 25

(2) INFORMATION FOR SEQ ID NO:4:

(i) SEQUENCE CHARACTERISTICS:
                (A) LENGTH: 25 base pairs
                (B) TYPE: nucleic acid
                (C) STRANDEDNESS: single
                (D) TOPOLOGY: linear (ii) MOLECULE TYPE: other nucleic acid (iii) HYPOTHETICAL: NO

(iv) ANTI-SENSE: YES (xi) SEQUENCE DESCRIPTION: SEQ ID NO:4:

CTCTCGCACC CATCTCTCTC CTTCT                                                 25